United States Patent
Milos-Schouwink et al.

(10) Patent No.: US 10,308,869 B2
(45) Date of Patent: Jun. 4, 2019

(54) LIQUID CONTAINING POLYMER MARKER, USE OF A POLYMER MARKER AS AUTHENTICATION TOOL, AND METHOD AND DEVICE FOR DETECTING A POLYMER MARKER DISSOLVED IN A LIQUID

(71) Applicant: SICPA HOLDING SA, Prilly (CH)

(72) Inventors: Mia Milos-Schouwink, Montreux (CH); Agnieszka Kapalka, Prilly (CH); Jean-Luc Dorier, Bussigny (CH); Lorenzo Sirigu, Lausanne (CH); Lucia Giovanola, Ivrea (IT); Paolo Schina, Turin (IT); Silvia Baldi, Samone (IT); Irma Disegna, Ivrea (IT); Silvano Tori, Ivrea (IT)

(73) Assignee: SICPA HOLDING SA, Prilly (CH)

( * ) Notice: Subject to any disclaimer, the term of this patent is extended or adjusted under 35 U.S.C. 154(b) by 49 days.

(21) Appl. No.: 15/509,680

(22) PCT Filed: Sep. 25, 2015

(86) PCT No.: PCT/EP2015/072110
§ 371 (c)(1),
(2) Date: Mar. 8, 2017

(87) PCT Pub. No.: WO2016/050637
PCT Pub. Date: Apr. 7, 2016

(65) Prior Publication Data
US 2018/0171217 A1 Jun. 21, 2018

(30) Foreign Application Priority Data
Sep. 30, 2014 (EP) ..................... 14187173

(51) Int. Cl.
*C09K 11/06* (2006.01)
*G01N 21/76* (2006.01)
(Continued)

(52) U.S. Cl.
CPC ........ *C09K 11/06* (2013.01); *B01L 3/502715* (2013.01); *B01L 3/502753* (2013.01);
(Continued)

(58) Field of Classification Search
CPC .......... C09K 11/06; G01N 21/76; G01N 1/18; G01N 1/00; B01L 3/502715; B01L 3/502753
(Continued)

(56) References Cited

U.S. PATENT DOCUMENTS 8,247,761 B1 * 8/2012 Agrawal ................ G06K 19/14
250/271
2003/0154647 A1 8/2003 Nguyen et al.
(Continued)

FOREIGN PATENT DOCUMENTS

WO 2007150030 12/2007
WO 2013101902 7/2013
(Continued)

OTHER PUBLICATIONS

"Generation of Functionalized and robust semiconducting polymer dots with polyelectrolytes", Yuhui et al, *Chem. Commun.*, 2012,48, 3161-3163.
(Continued)

*Primary Examiner* — Brian J. Sines
(74) *Attorney, Agent, or Firm* — Muncy, Geissler, Olds & Lowe, P.C.

(57) ABSTRACT

The present invention relates to markers for liquids that can be used to authenticate the origin and genuineness of a
(Continued)

Method of authentication of the marked organic liquid such as fuel according to Example 1 liquid, preferably a bulk liquid such as fuel. For this purpose, the present invention teaches the use of a polymer capable of forming a semiconducting polymer particle (pdot) in the liquid in small amounts. The invention encompasses a liquid comprising a) a polymer that is capable of forming a semiconducting polymer particle (pdot), the concentration of the polymer being 10 ppm by weight or less, and b) an organic substance in an amount of 90% by weight or more. The invention furthermore envisages the use of such a polymer as an authenticating marker in a liquid, preferably a fuel, and a method for authenticating the genuineness and/or origin of a liquid comprising a polymer capable of forming a semiconducting polymer particle (pdot), comprising the steps i. concentrating, isolating and/or extracting the polymer capable of forming a semiconducting polymer particle (pdot);
ii. aggregating the polymer or the polymer obtained in Step i. to form semiconducting polymer dots (pdots);
iii. irradiating the formed pdots with electromagnetic radiation capable of exciting the pdots to emit electromagnetic radiation by fluorescence and/or phosphorescence, and
iv. observing the electromagnetic radiation emitted in response to the exciting irradiation of step iii.

8 Claims, 8 Drawing Sheets

(51) Int. Cl.
| | |
|---|---|
| G01N 1/18 | (2006.01) |
| G01N 1/00 | (2006.01) |
| C10L 1/00 | (2006.01) |
| C10L 1/16 | (2006.01) |
| G01N 21/64 | (2006.01) |
| B01L 3/00 | (2006.01) |
| G01N 1/40 | (2006.01) |
| G01N 33/28 | (2006.01) |
| G01N 35/10 | (2006.01) |
| G01N 35/00 | (2006.01) |

(52) U.S. Cl.
CPC .............. *C10L 1/003* (2013.01); *C10L 1/165* (2013.01); *G01N 1/4005* (2013.01); *G01N 1/4077* (2013.01); *G01N 21/643* (2013.01); *G01N 21/6489* (2013.01); *G01N 33/2882* (2013.01); *G01N 35/10* (2013.01); *B01L 2200/0647* (2013.01); *B01L 2300/0681* (2013.01); *B01L 2300/1805* (2013.01); *B01L 2300/1894* (2013.01); *B01L 2400/06* (2013.01); *C09K 2211/1416* (2013.01); *C09K 2211/1425* (2013.01); *C10L 2230/16* (2013.01); *G01N 2001/4016* (2013.01); *G01N 2001/4088* (2013.01); *G01N 2021/6439* (2013.01); *G01N 2035/00207* (2013.01); *G01N 2035/00376* (2013.01); *G01N 2035/00445* (2013.01); *G01N 2035/00475* (2013.01)

(58) Field of Classification Search
USPC ..... 422/50, 68.1, 82.05, 82.08; 436/43, 164, 436/166, 174, 177, 178, 180
See application file for complete search history.

(56) References Cited

U.S. PATENT DOCUMENTS

| | | | |
|---|---|---|---|
| 2004/0067360 A1* | 4/2004 | Steenblik | G06K 19/06009 428/402 |
| 2005/0129580 A1 | 6/2005 | Swinehart et al. | |
| 2007/0225464 A1* | 9/2007 | Lewis | C08G 77/58 528/10 |
| 2008/0130018 A1* | 6/2008 | Steenblik | G06K 19/02 356/625 |
| 2008/0146744 A1 | 6/2008 | Ho et al. | |
| 2011/0278560 A1* | 11/2011 | Zhou | C08G 61/02 257/40 |
| 2012/0167666 A1* | 7/2012 | Nair | G03G 9/0825 73/38 |
| 2012/0282632 A1 | 11/2012 | Chiu et al. | |
| 2013/0234068 A1 | 9/2013 | Chiu et al. | |
| 2013/0266957 A1 | 10/2013 | Chiu et al. | |

FOREIGN PATENT DOCUMENTS

| | | |
|---|---|---|
| WO | 2013116614 | 8/2013 |
| WO | 2014031902 | 2/2014 |

OTHER PUBLICATIONS

"Multicolor conjugated Polymer dots for biological fluorescence imaging", Wu, *ACS Nano*, 2008, 2 (11), pp. 2415-2423.
"Highly fluorescent semiconducting polymer dots for single-molecule imaging and biosensing", Sun et al, SPIE 8812, Biosensing and Nanomedicine VI, 881205-1 to 881205-9 (Sep. 11, 2013).
International Search Report and Written Opinion issued with respect to application No. PCT/EP2015/072110.
Eurasia office action in counterpart Eurasian Application No. 201690336/31 dated Dec. 9, 2016 (and English language translation).

* cited by examiner

Figure 1. Examples of pdot precursors
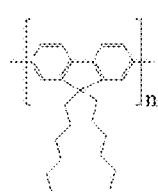
101
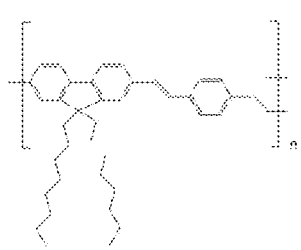
102
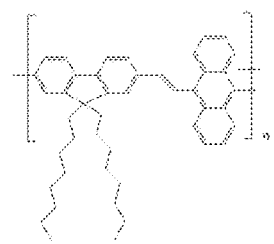
103

Figure 2. LOC design
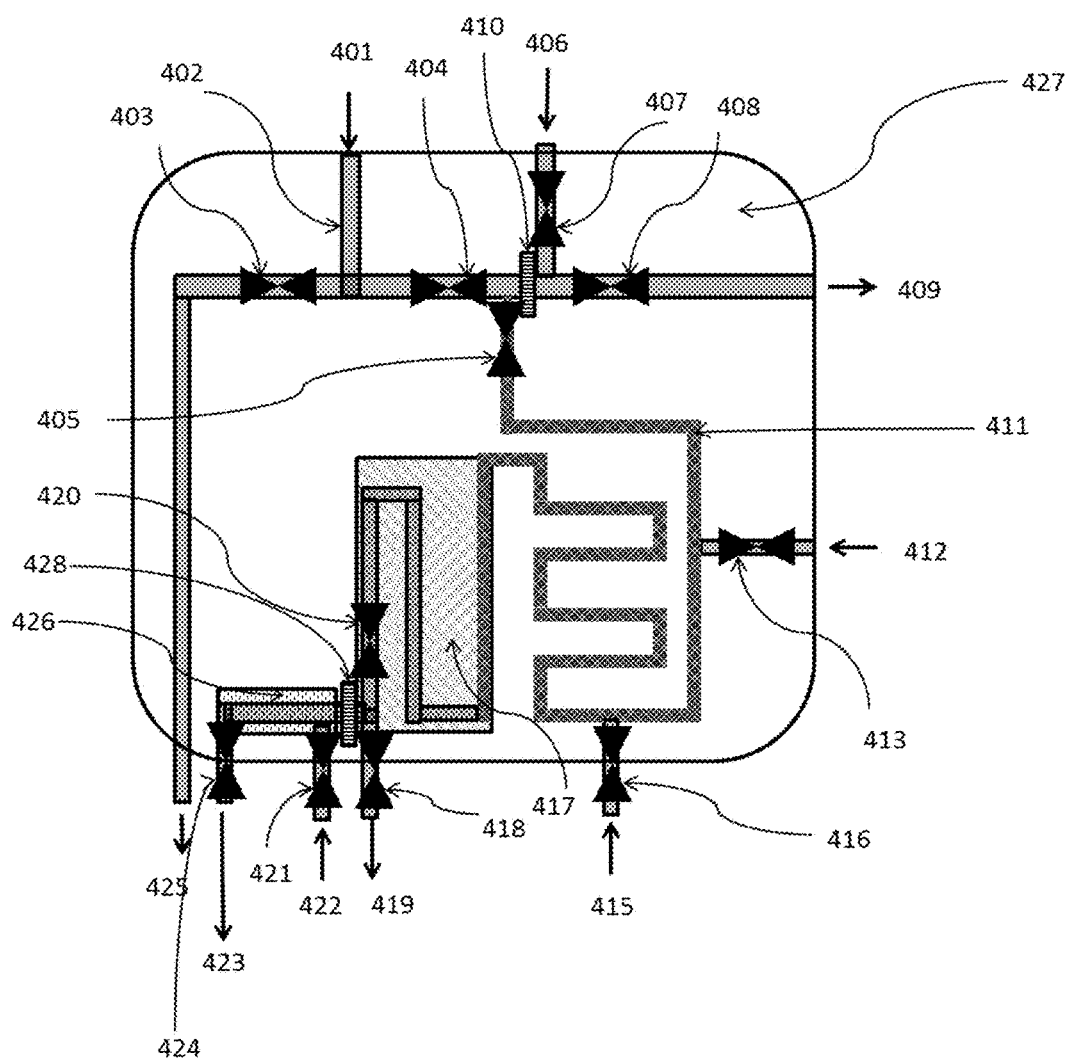

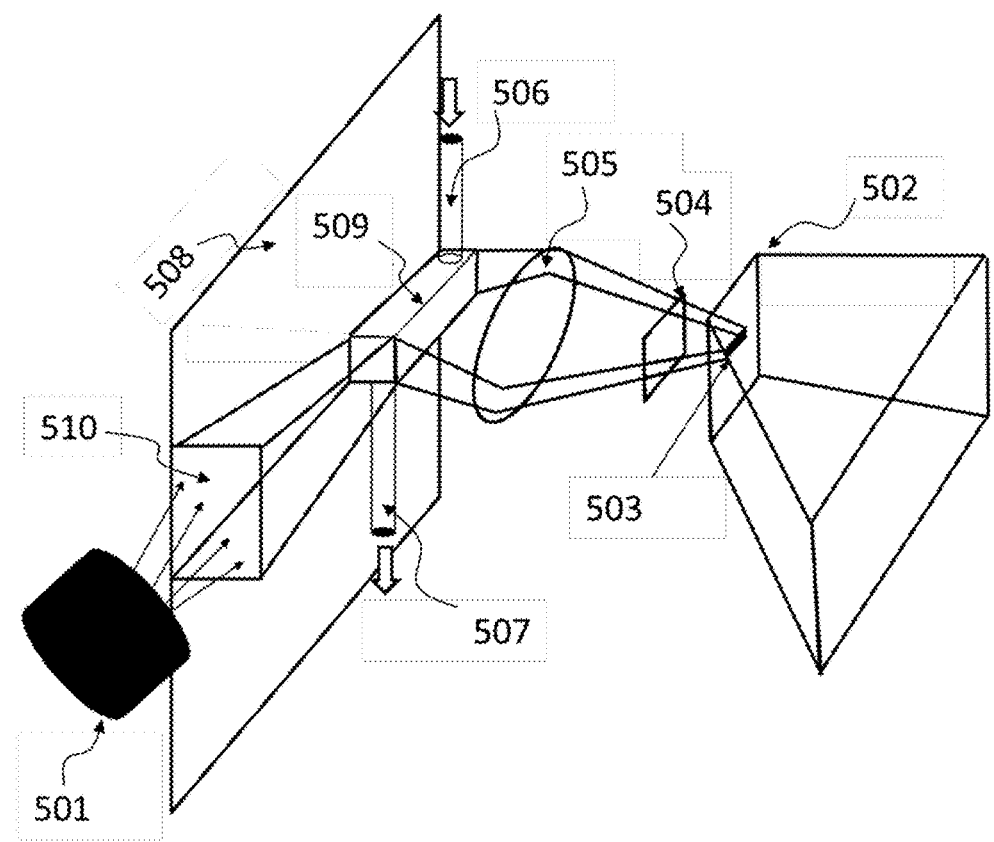
Figure 3. Detection set-up

Figure 5. Method of authentication of the marked organic liquid such as fuel according to Example 1
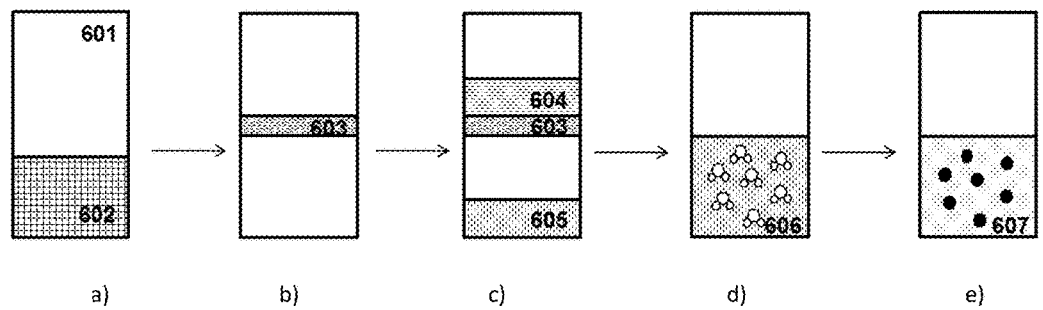
Figure 6. Luminescence shift according to Example 1.
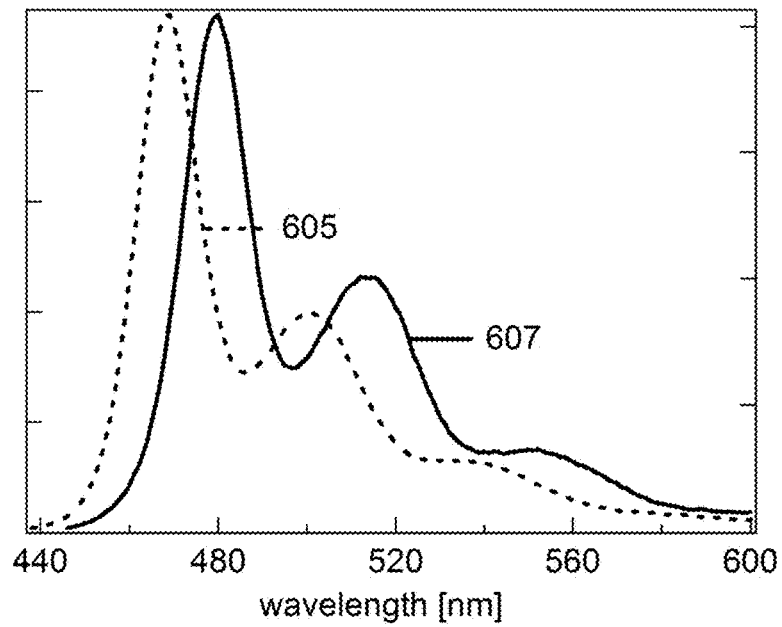

Figure 7. Method of authentication of the marked organic liquid such as fuel according to Example 2.
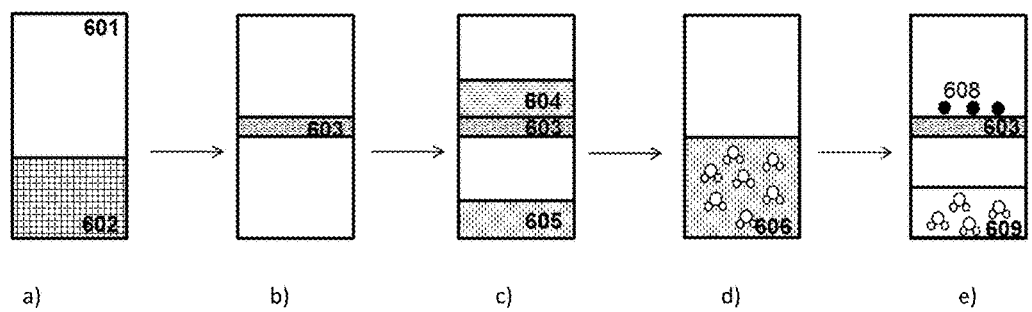
a)     b)     c)     d)     e)
Figure 8. Luminescence shift according to Example 2.
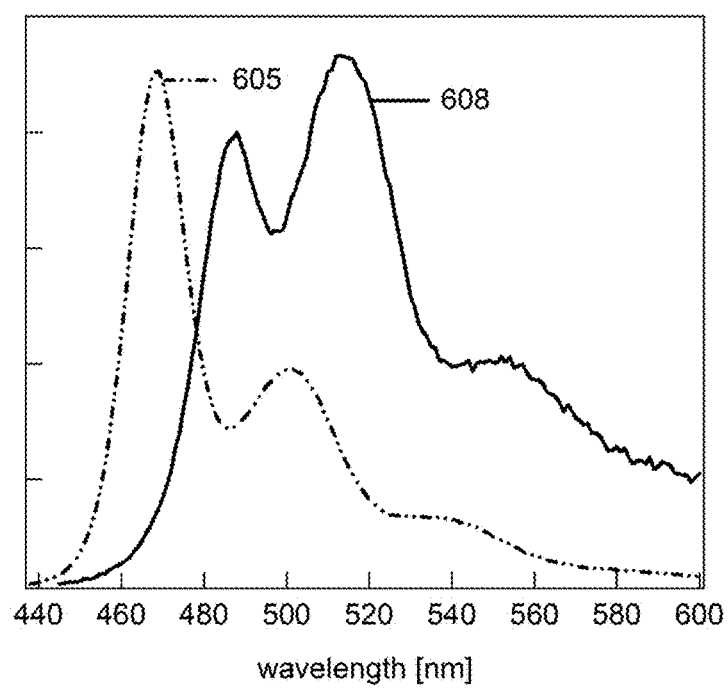

Figure 9. Method of authentication of the marked organic liquid such as fuel according to Example 3.
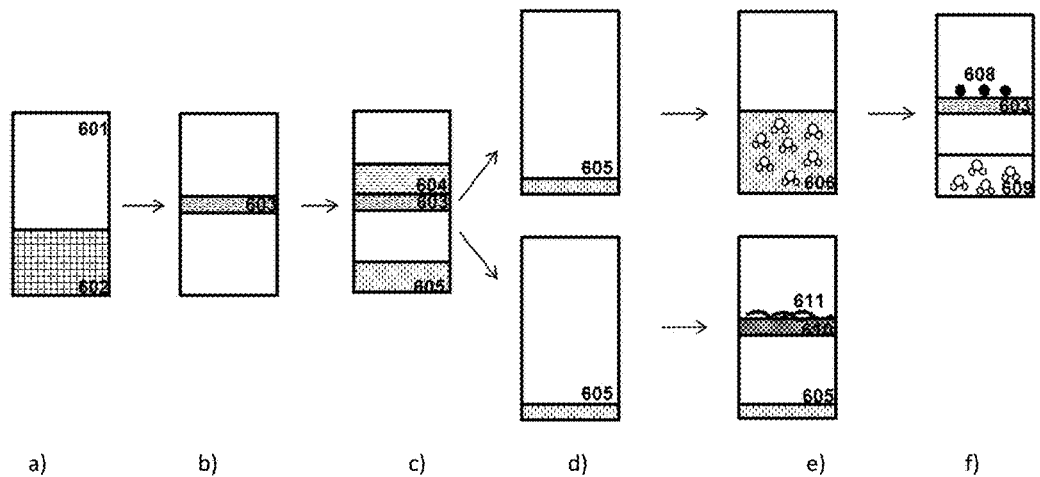
Figure 10. Luminescence shift according to Example 3.
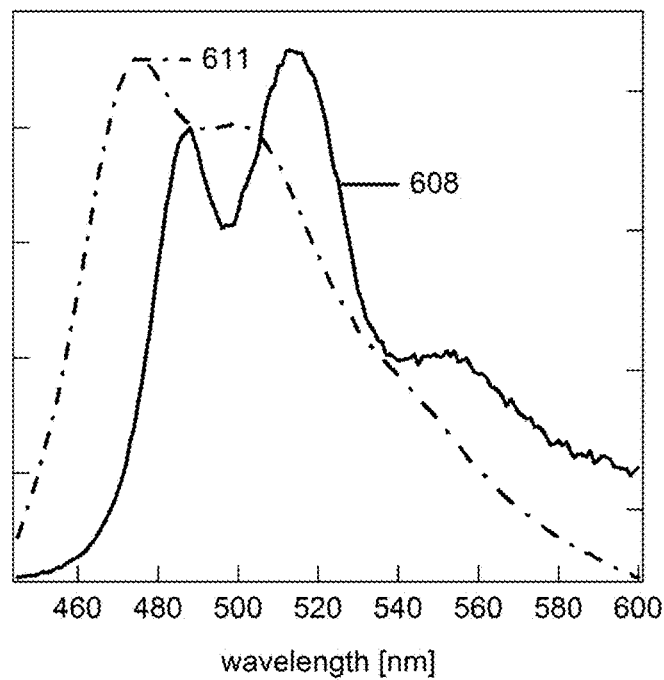

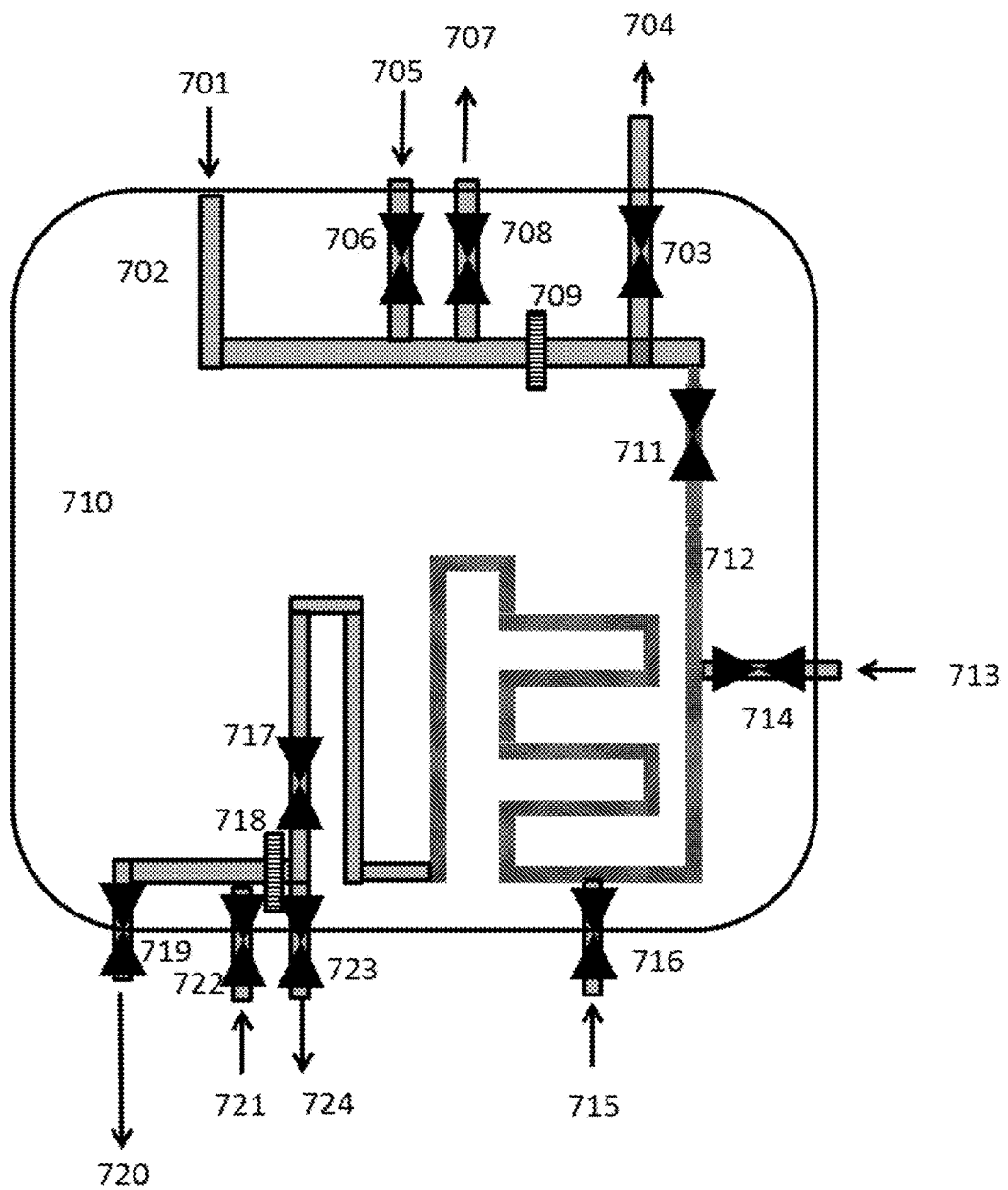
Figure 11. LOC design 2

LIQUID CONTAINING POLYMER MARKER, USE OF A POLYMER MARKER AS AUTHENTICATION TOOL, AND METHOD AND DEVICE FOR DETECTING A POLYMER MARKER DISSOLVED IN A LIQUID

TECHNICAL FIELD

The present invention is generally in the field of means for authenticating the origin and genuineness of a liquid, in particular a liquid fuel, and as such relates to a liquid containing a polymer marker, the use of a polymer marker as authentication tool, and a method and a device for detecting a polymer marker dissolved in a liquid.

BACKGROUND OF THE INVENTION

In many technical fields and areas of business, it is of great importance to verify that a given product is genuine. Non-genuine (imitated) products often suffer from poor quality and may damage the reputation of the manufacturer of the genuine product. Also, if the product is of relevance to the safety of a device, the use of an imitated product may lead to damages of a device or accidents.

Bulk liquids are generally more difficult to protect against imitations than solid products, which can be marked by signs, imprints or authentication marks. Small volumes of liquids can be bottled into specific sealed containers, which may then be marked accordingly. These techniques are however not available or not practicable for liquids that are handled in large quantities, such as fuels. Nonetheless, there is also a desire that such liquids be verifiable as genuine product.

This can generally be achieved by adding a specific substance, also referred to as "marker", in a small quantity. The marker can then be detected by someone wishing to verify the genuineness and authenticity of a product. For instance, it is common practice to add coloring substances, such as dyes, to fuels in order to mark them as genuine brand product.

Yet, the simple color impression obtained by such markers can easily be reproduced by forgers by combining known ingredients, considering that a large number of dyes are commercially available. Further, an identity check that goes beyond a mere visual inspection by the naked eye is difficult to perform on the spot and e.g. at the place of delivery, and usually a time-consuming check of a sample of a delivered liquid in a laboratory needs to be conducted in order to obtain certainty that a delivered liquid is genuine.

There thus is a need for an improved marker that is difficult to forge and that can be easily inspected by a small device e.g. at the place of delivery. Further, such a marker is preferably not visible by inspection with the naked eye, so that a complicated chemical analysis is required to obtain the precise chemical structure of the marker. This represents a further difficulty for counterfeiters, as the necessary equipment such as NMR, HPLC etc. is typically not readily available to counterfeiters. Such a marker is further preferably detectable in minute amounts, so that the marking can be effected efficiently and cheap, while still providing a suitable response that can be detected by small testing devices without the need for highly sophisticated test equipment.

In the medicinal and biological field, semiconducting polymer particles (pdots) have been the subject of research, as they are interesting as nanoprobes due to their non-toxicity, bright photoluminescence, high photostability and fast emission rates. They have mainly been used as in biological applications, such as in biological fluorescence imaging and sensing. The formation of semiconducting polymer particles (pdots), in particular those showing fluorescence and/or phosphorescence, is described in a large number of prior art documents. These include for instance:

"Generation of Functionalized and robust Pdots . . . ", Yuhui et al, *Chem. Commun.*, 2012, 48, 3161-3163;

"Multicolor conjugated Pdots for biological fluorescence . . . ", Wu, *ACS Nano*, 2008, 2 (11), pp 2415-2423; and "Highly fluorescent pdots for single-molecule . . . ", Sun et al, SPIE 8812, Biosensing and Nanomedicine VI, 881205 (11 Sep. 2013).

Further information on the preparation and properties of various kinds of pdots can be found in various patents and patent applications, such as US 2012 0282632; US 2013 0266957; WO 2013 116614; US 2008 0146744; US 2013 0234068; and WO 2013 101902, all of which are herewith incorporated by reference.

In the prior art, pdot formation and detection is carried out using bench laboratory equipment, which is big and expensive. Moreover, their operation may require skilled people and the performed analysis can be time-consuming. This limited the application of pdots, and they were thus not considered to represent a possible solution to the problem discussed above with respect to the marking of liquids.

In view of the above, an object of the invention is to provide a solution to the problems formulated above. In particular, it is an object of the present invention to provide a marker for liquids that can easily be identified even when present in only small quantities, and which provides unique identification characteristics that can be analyzed without the need for complicated laboratory equipment, as well as a liquid marked therewith. It is a further object of the invention to provide a liquid protected against counterfeiting by inclusion of a marker, wherein the marker is not visible with the naked eye.

It is a further object of the present invention to provide a cheap and portable solution for the detection of specific markers that can be dissolved in a liquid at low concentration, in particular in fuel liquids, such as refined petroleum products including gasoline, diesel, kerosene, etc. The markers preferably have a good solubility in the liquid, and preferably are difficult to be identified, extracted and separated.

The proposed solutions preferably provide a fast and reliable detection of the presence of a marker inside a liquid, such as liquid fuel.

SUMMARY OF THE INVENTION

The mentioned problems and objects are solved by the following items and as specified in the claims. Further aspects and embodiments will become apparent from the following detailed description of the invention.

1. Method for authenticating the genuineness and/or origin of a liquid comprising a polymer capable of forming a semiconducting polymer particle (pdot), comprising the steps
   i. concentrating, isolating and/or extracting the polymer capable of forming a semiconducting polymer particle (pdot);

ii. aggregating the polymer obtained in Step i. to form semiconducting polymer dots (pdots);
iii. irradiating the formed pdots with electromagnetic radiation capable of exciting the pdots to emit electromagnetic radiation by fluorescence and/or phosphorescence, and
iv. observing the electromagnetic radiation emitted in response to the exciting irradiation of step iii.

2. Method according to item 1, wherein the liquid is a fuel and wherein the concentration of the polymer capable of forming a semiconductor particle is equal to or less than 10 ppm by weight.

3. Method according to any one of items 1 and 2, wherein the method is implemented in a portable device.

4. Method according to any one of items 1 to 3, wherein the aggregation of the polymer to form pdots is performed by re-precipitation using water and a water-miscible organic solvent; or by mini-emulsion using two or more non-miscible solvents and a surfactant.

5. Method according to any one of items 1 to 4, which is performed in a lab-on-chip detection device (427) comprising the following steps:
    a) Introducing an amount of liquid containing a polymer capable of forming a semiconducting polymer dot (pdot), preferably 10 ml or less, into the lab-on-chip (427) at an entry (401) and via a microfluidic channel (402);
    b) analyzing the liquid fluorescence background of the introduced liquid at an exit (425);
    c) filtering the introduced liquid through a size and/or chemical affinity exclusion membrane (410) in order to increase the concentration of the polymer and to produce a mixture A;
    d) Introducing into the lab-on-chip (427) at an entry (406) an amount of organic solvent, preferably in an amount <0.5 ml, to be added to mixture A to dissolve and extract the polymer;
    e) optionally, introducing into the lab-on-chip (427) at an entry (412) an amount of a polymeric additive in an organic solvent, preferably in an amount <10 ul, or a surfactant solution in water, for example a micellar solution, to be added to mixture A;
    f) optionally, homogenizing the so obtained mixture A through a microfluidic channel (411) exhibiting mixing structure and/or capability;
    g) introducing into the lab-on-chip (427) at an entry (415) an amount of water, preferably in an amount <10 ml, to be added to mixture A, in order to promote the aggregation of the polymer to produce the pdots;
    h) heating the so obtained mixture A flowing over a local heating region (417), in order to concentrate mixture A by evaporating the organic solvent;
    i) filtering the so obtained mixture A through a size-exclusion membrane (428), to retain the so formed Pdots on the membrane (428);
    j) optionally, collecting the so generated organic solvents and water free of Pdots in a reservoir (423), while being cooled at a local cooling plate (426);
    k) Introducing into the lab-on-chip (427) at an entry (422) an amount of water, to collect the Pdots retained on the membrane (428), in order to form an aqueous dispersion B comprising said Pdots and to transport said Pdots to a preferably optically transparent collector (419, 509) in the form of an aqueous dispersion B;
    l) analyzing the so obtained aqueous dispersion B in the collector (419, 509) with a fluorescence detecting device (502), preferably a spectrometer or silicon photodiode, in order to detect the so extracted and produced Pdots and their fluorescence.

6. Method according to any one of items 1 to 5, which additionally comprises the following steps:
    iii.a. irradiating the polymer capable of forming a semiconducting polymer particles, or a solution containing it, with electromagnetic radiation capable of exciting the polymers to emit electromagnetic radiation by fluorescence and/or phosphorescence, and
    iv.a. observing the electromagnetic radiation emitted in response to the exciting irradiation of step iii.a.

7. The method according to item 6, which comprises further a step of comparing the electromagnetic radiation emitted by the polymer observed in step iv.a with the electromagnetic radiation emitted by the pdot observed in step iv.

8. The method according to item 6 or item 7, wherein the polymer irradiated in step iii.a is present in a liquid to be evaluated for its genuineness and/or origin, is present in a water-soluble solvent other than the liquid to be evaluated for its genuineness and/or origin, or is present undissolved on a supporting surface.

9. Method according to any one of items 1 to 8, wherein the polymer capable of forming a semiconducting polymer dot (pdot) contains a structural unit selected from structural units comprising a (9, 9, dioctyl-2,7-divinylenefluorenylene)-alt-co-(9,10-anthracene) moiety of formula (1) and structural units comprising a moiety of formula (102):

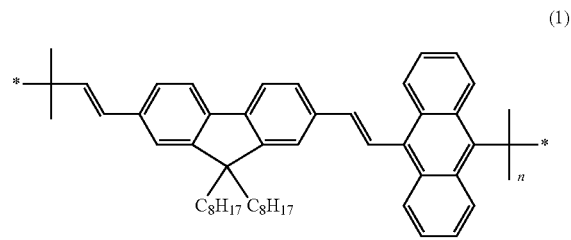

(1)

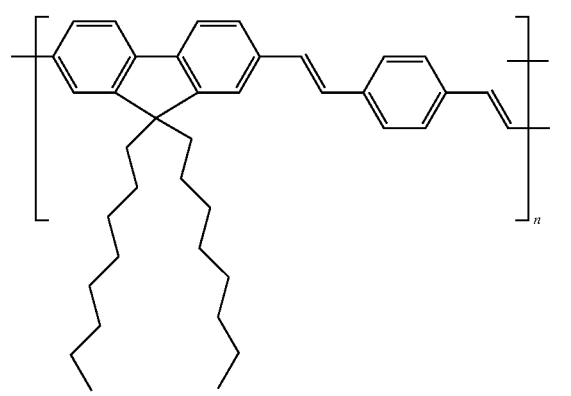

(102)

10. A lab-on-chip detection device (427) suitable to detect a polymer capable of forming a semiconducting polymer dot (pdot) dissolved in a liquid, preferably a fuel, comprising:
    a first entry (401) and a first microfluidic channel (402) for introducing an amount of said liquid into the lab-on-chip (427);
    a first membrane (410) for receiving said liquid from said first microfluidic channel (402) via a first valve (404) and for filtering said liquid in order to increase the concentration of the polymer and to produce a first mixture (A);

a second entry (406) for introducing into the lab-on-chip (427) via a second valve (407) an amount of organic solvent to be added to said first mixture (A) to dissolve and extract the polymer in a channel (411);

a third entry (415) for introducing into the lab-on-chip (427) via a third valve (416) an amount of water, to be added to said first mixture (A) and said amount of organic solvent, in order to form a second mixture in said channel (411) and to promote therein the aggregation of the polymer and to produce the pdots;

optionally, a local heating region (417) for heating said second mixture received from said channel (411), in order to concentrate said second mixture by evaporating the organic solvent;

a second membrane (428), for receiving the concentrated second mixture via a fourth valve (420) and for filtering the concentrated second mixture to retain the so formed Pdots on the second membrane (428);

a fourth entry (422) for introducing into the lab-on-chip (427) via a fifth valve (421) a small amount of water, to collect the pdots retained on the second membrane (428), in order to form an aqueous dispersion (B) comprising said pdots and to transport said pdots to a preferably optically transparent collector (419, 509) in the form of said aqueous dispersion (B);

a fluorescence detecting device (502), for analyzing the so obtained aqueous dispersion (B) in the collector (419, 509), in order to detect the so extracted and produced Pdots and their fluorescence and a lab-on-chip controller configured to:
operate said first valve (404) so as to let pass said liquid through said first membrane (410) and to produce said first mixture (A);
operate said second valve (407) so as to add said amount of organic solvent to said first mixture (A);
operate said third valve (416) so as to add said amount of water to said first mixture (A);
operate said local heating region (417) so as to heat said second mixture;
operate said fourth valve (420) so as to filter the concentrated second mixture; and to
operate said fifth valve (421) so as to collect the pdots retained on the second membrane (428) and to transport said pdots to said collector (419, 509).

11. The lab-on-chip detection device (427) according to item 10, further comprising an entry (412) for introducing into the lab-on-chip (427) an amount of a polymeric additive diluted in an organic solvent to be added to the first mixture (A) to functionalize the polymer.

12. The lab-on-chip detection device (427) according to item 10 or 11, wherein said channel (411) is adapted to exhibit a mixing structure and/or capability for homogenizing the obtained second mixture.

13. The lab-on-chip detection device (427) according to any one of items 10 to 12, further comprising a reservoir (423) for collecting the so generated organic solvents and water free of Pdots, while being cooled at a local cooling plate (426).

14. The lab-on-chip detection device (427) according to any one of items 10 to 13, wherein the first membrane (410) is a size and/or chemical affinity exclusion membrane.

15. The lab-on-chip detection device (427) according to any one of items 10 to 14, wherein the second membrane (410) is a size-exclusion membrane.

16. The lab-on-chip detection device (427) according to any one of items 10 to 15, wherein the fluorescence detecting device (502) is a spectrometer or silicon photodiode.

17. A system comprising:
A. a detection device according to any one of items 10 to 16;
B. a liquid, preferably a fuel;
C. a polymer capable of forming a semiconductor polymer dot dissolved in the fuel with a concentration of equal to or less than 10 ppm by weight, more equal to or less than 1 ppm by weight.

18. The system according to item 17, wherein the polymer contains a structural unit derived from [(9, 9, dioctyl-2,7-divinylenefluorenylene)-alt-co-(9,10-anthracene)] as represented by the following formula (1):

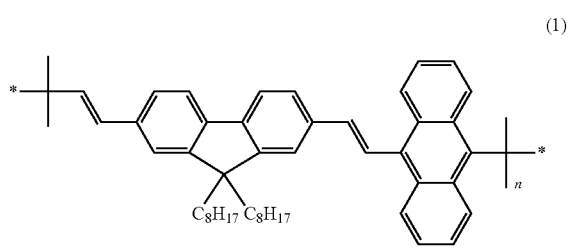

(1)

BRIEF DESCRIPTION OF THE DRAWINGS

Embodiments of the present invention, which are presented for better understanding the inventive concepts and which are not to be seen as limiting the invention, will now be described with reference to the figures:

FIG. 1 illustrates examples of pdot precursors.
101: Poly[(9,9-dihexyl-2,7-fluorenyl-2,7-diyl)]
102: Poly[(9,9-dioctyl-2,7-divinylenefluorenylene)-alt-co-(1,4-phenylene)]
103: Poly [(9, 9, dioctyl-2,7-divinylenefluorenylene)-alt-co-(9,10-anthracene)]
FIG. 2 illustrates a Lab-On-Chip Design.
401: Entrance for marked fuel
402: microfluidic channel
403: one way valve for analysis of the real fuel background
404: one way valve involved in the conjugated polymer separation phase
405: one way valve involved in the conjugated polymer extraction phase
406: Entrance of organic solvent (THF for reprecipitation procedure, Toluene for miniemulsion procedure)
407: one way valve involved in the conjugated polymer extraction phase
408: one way valve involved in the conjugated polymer separation phase
409: exit of fuel with reduced conjugated polymers
410: membrane (chemical affinity or size exclusion)
411: microfluidic channel with mixing structure/capabilities
412: entrance of additives (for example 10 ppm solution of PSMA for reprecipitation procedure, and micellar surfactant solution for mini-emulsion procedure)
413: one way valve involved in the Pdot formation phase
415: Entrance of pure water
416: one way valve involved in the Pdot formation phase
417: local heating plate
418: one way valve involved in the Pdot collection phase
419: Collection of Pdots in aqueous solution
420: one way valve involved in Pdot collection phase
421: one way valve involved in the Pdot extraction phase (extraction from membrane)

422: entry of water for Pdot extraction phase (extraction from membrane)
423: exit of "free" water and rests of organic solvent aimed for recycling
424: one way valve aimed for recuperation of solvents
425: exit of non-transformed fuel, aimed for the analysis of the real background
426: local cooling plate
427: chip substrate
428: membrane (chemical affinity or size exclusion)
FIG. 3 illustrates a detection set up.
501: Light source (LED, laser, . . . )
502: Spectrometer (light dispersing arrangement with detector unit)
503: Entrance slit (of the spectrometer)
504: Filter (long-pass, band-pass)
505: Collection lens (lens arrangement)
506: In-flow channel/pipe of the collection cuvette (509)
507: Out-flow channel/pipe of the collection cuvette (509)
508: Lab on Chip board/plane
509: Collection cuvette
510: Irradiation light guide
FIG. 5 illustrates method steps employed in Example 1 of the present application.
601 Flask
602 Mixture of a water soluble solvent and the liquid to be evaluated for its genuineness and/or origin
603 Chemical affinity membrane
604 Liquid to be evaluated for its genuineness and/or origin
605 Water-miscible solvent containing pdot precursor (polymer)
606 Mixture of water and water-miscible solvent containing pot precursor
607 Pdot dispersion
FIG. 6 illustrates a luminescence shift according to Example 1 of the present application.
605 Luminescence Emission spectrum obtained from the water-miscible solvent containing pdot precursor (polymer)
607 Luminescence Emission spectrum obtained from the dispersion of pdots
FIG. 7 illustrates method steps employed in Example 2 of the present application.
601 Flask
602 Mixture of a water soluble solvent and the liquid to be evaluated for its genuineness and/or origin
603 Chemical affinity membrane
604 Liquid to be evaluated for its genuineness and/or origin
605 Water-miscible solvent containing pdot precursor (polymer)
606 Mixture of water and water-miscible solvent containing pot precursor
608 Pdots
609 Mixture of water and water-miscible solvent
FIG. 8 illustrates luminescence shift according to Example 2 of the present application.
605 Luminescence Emission spectrum obtained from the water-miscible solvent containing pdot precursor (polymer)
608 Luminescence Emission spectrum obtained from pdots
FIG. 9 illustrates method steps employed in Example 3 of the present application.
601 Flask
602 Mixture of a water soluble solvent and the liquid to be evaluated for its genuineness and/or origin
603 Chemical affinity membrane
604 Liquid to be evaluated for its genuineness and/or origin
605 Water-miscible solvent containing pdot precursor (polymer)
606 Mixture of water and water-miscible solvent containing pot precursor
608 Pdots
609 Mixture of water and water-miscible solvent
610 Membrane
611 Polymer (pdot precursor)
FIG. 10 illustrates luminescence shift according to Example 3 of the present application.
608 Luminescence Emission spectrum obtained from pdots
611 Luminescence Emission spectrum obtained from polymer (pdot precursor)
FIG. 11 illustrates a Lab-On-Chip Design.

DETAILED DESCRIPTION

Definitions of Terms

Figure 4:
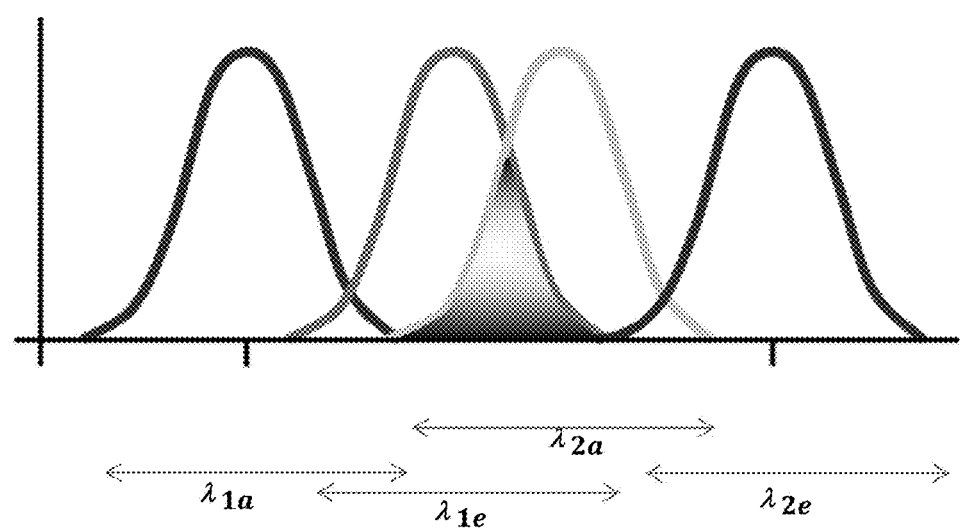
FIG. 4 illustrates the energy transfer of donor and acceptor. The figure describes the relationship between the excitation wavelength range of a donor ($\lambda 1a$), the emission wavelength range of a donor ($\lambda 1e$), the excitation wavelength range of an acceptor ($\lambda 2a$) and the emission wavelength range of an acceptor ($\lambda 2e$).

In the present invention, the term "comprising" is used open-endedly, such that the recited features are necessarily present, and other features may be present in addition. Yet, the term "comprising" also includes the more restrictive meanings of "consisting of" and "consisting essentially of".

The term "one or more" is used to denote that at least one of the recited features or compounds is present. The term however also includes the possibility that more than one of the recited features are present, such as two, three, four, five or six.

The term "polymer" is used to denote a chemical substances that is formed by reaction of one or more of the same (homopolymer) or different (copolymer) species. A polymer is formed from at least five, preferably at least 10 molecules of monomer. In another definition, a polymer in the sense of the present invention has a weight-average molecular weight (as measured using Gel Permeation Chromatography using a Polystyrol standard) of at least 500, preferably at least 1,000.

In cases of a copolymer, the copolymer may be a random copolymer, a block copolymer or a graft copolymer.

In the present invention, all explanations are given with respect to standard conditions (pressure: 1 atm, temperature: 20° C.). Accordingly, the term "liquid" refers to a substance that is liquid at 20° C.

In the following description, all values and proportions are by weight, unless specified differently.

The term "fuel" relates to a liquid in the above sense that is commonly used as fuel for combustion engines, and includes diesel, kerosene, gasoline, and liquid petroleum.

The term "hydrocarbon" is used to denote substances that consist completely of carbon and hydrogen atoms. Preferred examples of hydrocarbons are alkanes, alkenes and aromatic compounds, preferably those having 6 to 22 carbon atoms.

Polymer Capable of Forming a Semiconducting Polymer Particle (Pdot)

An essential element of the present invention is the use of a polymer that is capable of forming a semiconducting polymer particle (pdot). This polymer may also synonymously be referred to as pdot precursor or as polymer marker.

It is a necessity for the present invention that the pdot formed by the pdot precursor exhibits fluorescence and/or phosphorescence. This allows verifying the authenticity of the marker/the liquid by irradiating the formed pdot with excitation radiation and measuring the emission emitted by the pdot in response to the excitation radiation. While this is not strictly a requirement, it is therefore typically the case and hence preferable that the pdot precursor is a phosphorescent and/or fluorescent material, more preferably a fluorescent material. Even more preferably, the pdot precursor has a delocalized, conjugated π system.

The pdot precursor is a polymer that is formed from one or more monomers. More preferably, the pdot precursor is a copolymer of at least two monomers, and further preferably is a block copolymer of two or more (such as three or four) copolymer blocks. Alternatively, the pdot precursor can be a graft copolymer wherein monomers, oligomers or polymers made from one or more monomers having a conjugated π system and exhibiting fluorescence and/or phosphorescence is/are grafted on a preformed polymer.

In one particularly preferred aspect, the pdot precursor is a diblock copolymer having one essentially hydrophobic block made from one or more hydrocarbon monomers, e.g. selected from the group consisting of ethylene, propene, butene, hexane, octane and styrene, and one copolymer block that is substantially more hydrophilic. Such a substantially more hydrophilic copolymer block may be prepared from monomers having heteroatoms, such as nitrogen or oxygen atoms, and may be prepared from alkylene oxides or diols, such as ethylene oxide or propylene oxide, lactams, unsaturated esters and carboxylic acids, etc.

In either case, the pdot precursor needs to contain a fluorescent moiety. The block copolymer thus contains at least one block that forms a fluorescent semiconducting polymer block having a conjugated π system. This may be either the hydrophobic or the less hydrophobic polymer block, and is preferably the less hydrophobic polymer block.

Such a block copolymer having a hydrophobic and a less hydrophobic block may be particularly useful as a pdot precursor if the liquid is a hydrophobic substance, such as a fuel, as then the hydrophobic copolymer block derived from e.g. one or more hydrocarbon monomers provides solubility in the liquid. Further, the copolymer block that forms a fluorescent semiconducting polymer block having a conjugated π system is typically relatively less lipophilic. In consequence, the pdot precursor aggregates (self-assembles) into a micelle-like structure when brought into contact with a less lipophilic solvent, e.g. water, thereby aggregating to form a pdot.

Any polymer having a conjugated π system can be used as marker in the fuel as long as it is soluble/dispersable. Light emitting polymers/conjugated polymers that can be used as pdot precursors to carry out the invention include polymers comprising units selected from the following:
Poly(1,4-phenylene vinylene) (PPV) and its derivatives
Poly(1,4-phenylene) (PPP) and its derivatives
Polyfluorene (PFO) and its derivatives
Poly(thiophenes)
Nitrogen-containing polymers
Poly [(9, 9, dioctyl-2,7-divinylenefluorenylene)-alt-co-(9, 10-anthracene)]

Preferably, polymers without heteroatoms such as N, S are used for the fuel marking.

In principle, any monomer having a fluorescent moiety can be used for the production of the pdot precursor. Such fluorescent moieties can for instance be selected from those typically used as emitters in OLED (Organic Light Emitting Device) applications. Functionalizing these into polymerizable species and preparing (co)polymers therefrom is a routine task for the skilled person, as standard organic chemistry can be employed.

Further, many polymers that are such fluorescent emitters are commercially available, e.g. from H.W. Sands Corporation in the OPA series of products. These include e.g. Poly(2,5-dioctyl-1,4-phenylene)-end capped with DMP (available from H.W. Sands Corporation under the tradename OPA1103), Poly[(9,9-Dihexylfluorenyl-2,7-diyl)-co-(9,10-anthracene)] (available from H.W. Sands Corporation under the tradename OPA 1871), Poly[{9,9-dihexyl-2,7-bis(1-cyanovinylene)fluorenylene]-alt-co-[2,5-bis(N,N'-diphenylamino)-1,4-phenylene}] (available from H.W. Sands Corporation under the tradename OPA 2212), Poly[(9,9-dihexyl-2,7-(2-cyanovinylene)-fluorenylene)] (available from H.W. Sands Corporation under the tradename OPA 2267), Poly(9,9-dioctylfluoren-2,7-diyl)-End capped with DMP (available from H.W. Sands Corporation under the tradename OPA 2311), Poly[(9,9-dihexylfluorenyl-2,7-diyl)-co-(2,6-pyridine)] (available from H.W. Sands Corporation under the tradename OPA 2347), Poly[(9,9-dioctyl-fluorenyl-2,7-diyl)-co-(4,4'-(N-(4-sec-butylphenyl)) diphenylamine)] (available from H.W. Sands Corporation under the tradename OPA 2617), or Poly[(9,9-dihexylfluorenylene-2,7-divinylenefluorenylene)] (available from H.W. Sands Corporation under the tradename OPA 7758). The choice of a suitable fluorescent polymer or copolymer component allows tuning the desired excitation and emission spectra, and hence contributes to the security of the marking, making it more difficult to counterfeit.

The pdot precursor can be one of these or similar polymers, or can be prepared by coupling these polymers to a substantially hydrophobic copolymer block made from one or more selected from ethylene, propene, butene, hexane, octane or styrene, forming a block copolymer or graft copolymer. Also, the methods described by Kühne et al in « *Monodisperse conjugated polymer particles by Suzuki-Miyaura dispersion polymerization* » Nature Communications 3:1088 can be employed.

In one embodiment of the present invention, the pdot precursor is a semi conductive conjugated luminescent polymer. Examples of such semi-conductive conjugated luminescent polymers are those including a repeating unit shown in FIG. 1. Further pdot precursors that can be used in the present invention are described in US 2003/154647 A1, also incorporated herein by reference.

In order to have an efficient luminescence, the pdot precursor preferably contain at least 50% by mole and more preferably 80-90% by mole of repeating units having a moiety capable of showing fluorescence, e.g. those recited above as the fluorescent emitters recited above.

The liquid to be marked with the pdot precursor typically contains the pdot precursor in an amount of 10 ppm by weight or less, preferably 1 ppm by weight or less, and more preferably 500 ppb or less, but 100 ppb or more, preferably 200 ppb or more. Due to the concentration/isolation of the pdot from the liquid and the high quantum efficiency and the strong fluorescence and/or phosphorescence shown by the pdot formed by aggregation (self-assembly) of the pdot precursor, such small amounts are sufficient to enable a secure authentication.

In particular, a fuel can be marked at 500 ppb to 2 ppm with the pdot precursor. If the fuel is marked at 1 ppm, then, for example, 5 ml of fuel can be used for its authentication. On the other hand, if 500 ppb are used, then 10 ml of fuel can be used for authentication.

In order to increase further the complexity of the security solution for liquid marking, a polymer can be provided as a marker in the fuel that has the emission at a certain wavelength in the visible spectrum, such as in the range of 350-450 nm, 450-550 nm, or 550-650 nm.

Pdot Formation

In the use and the method of the present invention, the pdot precursor is separated and/or concentrated from the liquid, e.g. the fuel, wherein it is contained in small amounts, and then the pdot precursor is formed to a pdot. This occurs by self-assembly/aggregation of the pdot precursor polymer, forming a pdot. The pdot generally shows high quantum efficiency and fluorescence, typically due to intraparticle energy transfer.

After separation from the liquid containing the pdot precursor, this self-assembly and aggregation can be performed by techniques such as re-precipitation or mini-emulsion:

a) Re-precipitation

The non-aggregated pdot precursor is dissolved in a fully or partially water-miscible organic solvent, such as tetrahydrofuran (THF, viscosity of 0.48 cP at Room temperature, boiling point 66° C.). Also other solvents can be used, as long as they are fully or partially water miscible and capable of dissolving the pdot precursor. Examples of such solvents include ethers, such as THF, diethylether, ethylmethylether, ketones, such as acetone, methylethyl ketone, and cyclohexanone, and alcohols, such as methanol, ethanol, isopropanol, butanol etc. Fully water miscible solvents are preferred in order to avoid the formation of a biphasic system.

Further, additives such as hydrolysable polymers (e.g. starch polymers, lactic acid polymers) can be added in a certain amount (about 5-20% wt, preferably 5% wt with respect to the total weight of the composition). These will coordinate to the surface of the formed pdot and thus stabilize the nano-dispersion.

Then, water is added to thereby change the solvating properties of the solvent system. The amount of water is not critical, but needs to be sufficient to change the solvating properties enough in order to achieve self-assembly/aggregation of the pdot precursor to from the pdot. Typically, the amount of water is in the range of 1:1 to 3:1, as volume ratio water:polymer-solution of the pdot precursor in e.g. THF.

Upon addition of water, the chemical nature of the pdot precursor (hydrophobic interactions, π-π stacking) and of the optional polymeric additive cause an aggregation or self-assembly of the polymers. The aggregation/self-assembly is facilitated if the pdot precursor is a compound having hydrophobic and less hydrophobic portions, such as a block or graft copolymer. The hydrophobic portions will attract each other and will form a micelle-like structure with the hydrophobic portions present in the interior and the less hydrophobic (more polar) portion pointing towards the exterior.

The dispersion is then concentrated, typically by heating the dispersion (evaporation of solvents). The formed pdots are then analyzed with regard to their spectral properties (excitation at a certain wavelength $\lambda a$, emission at a different wavelength $\lambda e$).

b) Mini-emulsion (standard procedure)

The mini-emulsion uses two non-miscible solvents, such as water and a non-water miscible or poorly water-miscible solvent. Preferably, the mini-emulsion technique also employs a surfactant, for instance CTAB (cetyl-trimethyl-ammonium bromide) or SDS (sodium dodecyl sulphate), to produce an emulsion, that is added at the formation of the emulsion or which is previously added to water to be mixed with a solution of the pdot precursor in a non-watermiscible or poorly water miscible solvent. The surfactants are typically previously solubilized in water, with a concentration that is above their critical micellar concentrations (1 mM and 7-10 mM for CTAB and SDS, respectively).

Similarly as described for the re-precipitation technique, in a first step the pdot precursor isolated or extracted from the liquid is dissolved in a solvent, yet in this case a solvent that is not or only poorly miscible with water. The choice of solvent is not critical, as long as it can dissolve the pdot precursor and can form a biphasic system (an emulsion) with pure water or water containing some surfactant. Suitable solvents include aliphatic hydrocarbons, such as n-hexane or cyclohexane, aromatic hydrocarbons, such as toluene, benzene and ethyl benzene, aromatic amines, such as pyridine, halogenated solvents, such as dichloromethane and chloroform, and other non-water miscible solvents, such as acetonitrile.

The solution containing the pdot precursor is mixed with water or the micellar solution in water in order to form a dispersion. Finally, the obtained dispersion is heated to concentrate the dispersion and to remove the solvents, leading to the formation of pdots by self-assembly/aggregation of the pdot precursor. In cases where the pdot precursor contains a hydrophobic and a less hydrophobic (or hydrophilic) portion, such as in the case of a suitable block copolymer, the hydrophobic portion will orient towards the oil phase of the emulsion resulting from the solution of the pdot precursor in the non-water miscible or poorly water-miscible solvent, and the less hydrophobic (or hydrophilic) portion will orient towards the water phase.

The pdots formed by the above techniques show strong emission at a certain wavelength $\lambda e$ in response to excitation at different wavelength $\lambda a$. This can be tested without the need for large equipment using the apparatus and method described below. By providing the simple method for forming the pdots from the pdot precursor above and by providing the suitable and compact Lab-on-Chip described below, the present invention thus establishes a new authenticating means for the on-site testing of liquid with respect to its authenticity/genuineness.

The size of pdots formed with the two methods is slightly different; for the re-precipitation technique, the particles have typically diameters of 5-200 nm, while for the mini-emulsion technique, the particles have typically diameters of 40-500 nm (depending on the polymer and surfactant concentration in the solution mixture). The main difference is that the re-precipitation technique uses two miscible solvents and a mixing step, while the mini-emulsion uses two non-miscible solvents (organic solvent and water) and a surfactant to make emulsion (which is preferably an oil in water emulsion). Preferably, for analyzing a liquid that is a fuel, the re-precipitation method is used.

The fluorescent semiconducting polymer nanoparticles (pdots) formed according to the present invention are highly efficient fluorescent probes. The average diameter of Pdots can be very small, e.g. below 30 nm, when employing the suitable pdot formation technique.

Moreover, the interior of the pdots is preferably of hydrophobic character, in order to ensure the colloidal stability. This can be achieved by appropriately selecting the nature of the monomeric units of the pdot precursor, and this ensures that a densely packed fluorophore structure is formed upon self-assembly/pdot formation.

In the present invention, pdots are typically prepared via either one of two paths: mini-emulsion or re-precipitation. To further optimize the colloidal stability, the surface of Pdots can be functionalized with a polymer such as PSMA (poly styrene-co-maleic anhydride). The role of the last is to increase the charge on the surface, in order to decrease the electrostatic interactions between particles and thus to increase the colloidal stability. Any other copolymer that increases the charge on the surface can be used to functionalize/coat the Pdot. The coating/encapsulating/functionalizing agent should represent less than 20% of the Pdot precursor.

The Pdots are preferably able to be excited by irradiation with a wavelength between 250-800 nm, preferably 300-500 nm.

They are thus excitable with visible light, and emission can vary all over the visible spectrum. Pdots with emission in the blue spectrum exhibit narrow emission band (FWHM about 20 nm), while Pdots with emission in the red spectrum exhibit rather broad emission bands (FWHM about 100 nm). There is no restriction regarding the emission color; any type of Pdots can be used to carry out the invention.

Both the final pdot as well as the pdot precursor are fluorescent materials in that they emit light (typically in the visible spectrum) upon excitation by irradiation (typically in the UV or the visible spectrum). Yet, the excitation and emission properties of the pdot and the pdot precursor are not identical, as the formation of the pdot by self-assembly of the pdot precursor changes the electronic structure and/or the emission properties of the material. Accordingly, both excitation and emission of the pdot may be red-shifted (towards longer wavelengths) or blue-shifted (towards shorter wavelengths) as compared to the pdot precursor. The extent of this shift depends, besides others, also on the size and structure of the pdot, and is hence influenced by the reaction conditions employed for pdot formation. Since these are typically unknown to a counterfeiter and are not derivable from the liquid as such, the formation of pdots and the use of a pdot precursor provide an enhanced security level over small molecule emitters, such as fluorescent dyes.

Combinations of Donor and Emitter—Energy Transfer

In the use and the method of the present invention, also a combination of a pdot (formed from the pdot precursor) with a second material can be employed. For this purpose, a second component that is able to interact with the pdot in the sense of a donor or acceptor may be employed. Thereby, the security level can be improved, as a counterfeiter not only needs to identify the pdot precursor, but also the added second material in order to reproduce the spectral response (emission) that is observed upon irradiation with a certain excitation wavelength.

In detail, the pdot formed from the pdot precursor present in the liquid may act as a donor. This means that the excitation irradiation (from a light source) in a wavelength region $\lambda 1a$, in which the pdot can be excited, is absorbed by the pdot. The pdot then transfers the excitation energy by a radiation-free (FRET, Förster Resonance Energy Transfer) or radiative energy transfer in a wavelength region $\lambda 1e$ (emission wavelength region of the donor, i.e. the pdot in this case) to a second fluorescent species acting as acceptor. The acceptor has an excitation wavelength region $\lambda 2a$ that overlaps with the wavelength region $\lambda 1e$, and is thereby is excited to emit in wavelength region $\lambda 2e$. Herein, the wavelength ranges $\lambda 1e$ and $\lambda 2a$ must overlap in order to allow an energy transfer from the donor (the pdot) to the acceptor, while the respective emission ranges $\lambda 1e$ of the donor (pdot) and $\lambda 2e$ of the acceptor typically do not overlap, and are in different wavelength regions (see FIG. 4).

In consequence, by employing such a combination of components, it is possible to authenticate a material by irradiating the combination of pdot as donor and an acceptor in a wavelength region $\lambda 1a$, and to observe whether or not emission in a wavelength region $\lambda 2e$ occurs. This provides a particularly useful authentication means if the acceptor is added at the authenticating device and not part of the liquid (e.g. the fuel), as the nature of the acceptor dye is not derivable from the liquid as such.

On the other hand, the pdot formed from the pdot precursor may of course also act as acceptor. In this case, a donor dye (or pdot) may be added in the authenticating device (i.e. the Lab-on-Chip), followed by observing whether or not an emission from the pdot in the liquid occurs upon excitation of the added donor. In this case, the emission wavelength of the added donor must overlap with an excitation wavelength range of the pdot acceptor.

Authenticating Method and Device Therefor

The authentication method for authenticating the genuineness and/or origin of a liquid of the present invention comprises the following steps:
i. concentrating, isolating and/or extracting a polymer capable of forming a semiconducting polymer particle (pdot) present in the liquid to be tested for its genuineness and/or origin;
ii. aggregating the polymer obtained in Step i. to form semiconducting polymer dots (pdots);
iii. irradiating the formed pdots with electromagnetic radiation capable of exciting the pdots to emit electromagnetic radiation by fluorescence and/or phosphorescence, and
iv. observing the electromagnetic radiation emitted in response to the exciting irradiation of step iii.

Herein, the electromagnetic radiation observed in step iv. serves as indication of the genuineness and/or origin of the liquid. If the observed electromagnetic radiation conforms to a parameter that is defined as indicative for the genuineness and/or origin of the liquid (such as peak wavelength, shape of the spectrum, relative intensity ratio of emission at certain wavelengths, etc.), a decision as to the authenticity and/or origin of the liquid can be made. The exact kind and/or specific values and/or ranges of the parameter used for authentication purposes and indicative for genuineness and/or correct origin can be selected by a skilled person as a routine measure, similarly as in other well-established authentication methods relying on luminescent materials as markers, such as fluorescent dyes.

The retention itself of the formed Pdot on the size exclusion membrane (428, 603) may indicate authenticity, since conventional luminescent dyes would not be retained/stopped by the membrane. Measuring the luminescence of the Pdots retained on the size exclusion membrane firstly may indicate that the Pdot are present on the membrane and secondly may provide a parameter defined as indicative for the genuineness of the liquid. A first indication of the presence of the Pdot on the size exclusion membrane doesn't require necessarily a highly resolved emission spectrum, and may be thus very well adapted to a hand-held device detection.

Whether or not the electromagnetic radiation observed in step iv conforms to the selected parameter indicative for the genuineness and/or origin of the liquid depends on the chemical nature and constitution of the pdot and pdot precursor. Accordingly, since the pdot precursor is complex to synthesize and a specific pdot precursor used as a marker for an authentic liquid is difficult to reproduce exactly, the pdot precursor, respectively the formed pdot, is difficult to counterfeit. Besides others, if equipment having sufficient sensitivity is used for step iv, the observed radiation in step iv. may be distinguishable even for small variations in the pdot and the pdot precursor, such as different densities of luminescent (e.g. fluorescent and/or phosphorescent) moieties in the pdot or the pdot precursor, which will influence the intensity of the observed irradiation in step iv. Also, the molecular weight or molecular weight distribution might, for certain pdots and pdot precursors, influence the intensity and/or spectrum shape of the electromagnetic radiation observed in step iv. As reverse engineering is a highly complex and often impossible for polymers in the lack of knowledge about the exact synthesis conditions employed during the manufacture of the "authentic" pdot precursor, in particular as compared to small molecules such as fluorescent dyes, the method for the present invention can provide an improved level of security over conventional authentication methods relying on small molecule markers such as fluorescent dyes.

The authentication method of the present invention relies, in the above embodiment, on the electromagnetic radiation observed in step iv, as emitted by the formed pdot. In this embodiment, the luminescent properties of the pdot precursor are as such not a parameter that is used for authentication purposes. However, as already mentioned above, the pdot formation leads to different electronic properties of the pdot, e.g. emission properties upon excitation as a certain wavelength, as compared to the pdot precursor. For instance, the pdot formation leads to a red-shift or blue-shift (i.e. towards longer or shorter wavelengths) of the observed emission peak maximum.

In one embodiment, this change in properties can be used as an additional feature in the authentication method of the present invention. Accordingly in such an embodiment the method of the present invention additionally comprises the steps iii.a. irradiating the polymer capable of forming a semi-conducting polymer particles, or a solution containing it, with electromagnetic radiation capable of exciting the polymers to emit electromagnetic radiation by fluorescence and/or phosphorescence, and iv.a. observing the electromagnetic radiation emitted in response to the exciting irradiation of step iii.a.

Performing these additional steps then allows comparing the emission observed from the pdot in step iv. with the emission observed from the pdot precursor in step iv.a. The results of this comparison depend, on the one hand, on the chemical nature of the analyzed pdot precursor (or a material containing it) as described above, but on the other hand also on the chemical nature and identity of the pdot (or a material containing it). The latter, respectively the differences observed in the comparison, depend not only on the exact chemical species used as pdot precursor, but also on the reaction conditions employed for pdot formation, such as mini-emulsion and re-precipitation above, solvent choice for pdot precursor extraction, and possibly other process conditions.

The result of a comparison of the emission in the above steps iv and iv.a thus not only depend on the kind of pdot precursor (which may possibly be derived from a sample of authentic liquid by analysis), but also on the exact conditions used for pdot formation. While the former may be known or could be analyzed by a counterfeiter, the latter will only be known to the authentic manufacturer and/or the authority performing the method. Even if a counterfeit should by some way gain knowledge about the conditions employed by pdot formation, it represents an additional challenge for a counterfeiter not only to mimic the luminescent emission observed in step iv, but also to mimic the luminescent emission observed in step iv.a. This embodiment therefore provides an additional level of security.

The emission in step iv.a. of the pdot precursor may be observed prior to pdot formation, and may then be stored (e.g. in a computer) for later comparison with the emission observed in step iv. after pdot formation (subsequent observation of the emission in step iv and iv.a obtained from the same liquid sample before and after pdot material). Alternatively, a sample of liquid to be tested for authenticity may be partitioned into two sub samples, and only one of the subsamples is subjected to pdot formation. The subsamples may then be analyzed simultaneously (in parallel) or subsequently, and one may then compare the emission from the pdot precursor obtained in step iv.a with the emission observed in step iv (after concentrating, isolating, and/or extracting the pdot precursor and aggregating/pdot formation) and use the result of the comparison as means for indicating the authenticity and/or origin of the tested liquid. Specific embodiments of different ways for sample preparation and for comparing the emission observed in step iv and step iv.a are illustrated in the Examples and FIGS. 5 to 10.

The difference identified in the comparison of the emission observed in step iv and step iv.a (caused by the pdot and the pdot precursor, respectively) that is used as a criterion for evaluating the genuineness and/or origin of the liquid is not particular limited and can be freely selected by the skilled person. In one embodiment, the difference is the intensity of the observed emission at a certain wavelength. In another embodiment, the difference is the wavelength of the emission peak maximum (blue-shift or red-shift for step iv in comparison to step iv.a). The criterion can however also be more complex, such as a difference in the emission intensity ratios at defined wavelengths (e.g. 450 and 600 nm) for the emission observed in step iv and in step iv.a.

In one embodiment of the present invention, the method is implemented in a portable device. In the following the following terms are used as synonyms: MEMS (MicroElectroMechanical Sytems), LOC (Lab on a chip), µTAS (micro Total Analysis Systems).

According to an embodiment of the present invention, a method is proposed to detect on a lab-on-chip detection device (427) a polymer marker (pdot precursor) dissolved in a liquid, preferably a fuel, comprising the following steps:
(i) separation of a pdot precursor from a liquid, such as a fuel, in an LOC (lab-on-chip);
(ii) formation of pdots (self-assembly or aggregation of pdots precursors) in LOC;
(iii) automatic (in-situ) detection of pdots fluorescence and data reporting.

The method can be employed in a batch wise manner by analyzing a sample of the liquid, but can also be employed semi-continuously or continuously. It may also be adapted as an in-line quality control measure.

To achieve formation of pdots in the LOC (i.e., self-assembly/aggregation of the pdot precursor polymers), the standard procedures for pdot formation employed in the prior art had to be modified. In fact, several common steps of pdots formation, described in literature (e.g., N2 bubbling, sonication), cannot be performed in LOC. The present invention solves these problems by the pdot formation techniques developed by the present inventors and described above (mini-emulsion or re-precipitation).

In order to suppress or eliminate the fuel background fluorescence, as well as to prevent pdots from contamination with side molecules (i.e., prevent incomplete precursor folding) it is generally preferable to separate the pdot precursors from fuel in LOC. In this case, not only the presence, but also the quantity of the pdot precursor in a sample to be analyzed (e.g. 10 or 1 ml), as represented by e.g. the intensity of the emission observed from the formed pdot upon excitation, provides an authentication means.

According to an embodiment of the present invention, a method is proposed to detect on a lab-on-chip detection device (427) a polymer marker (pdot precursor) dissolved in a liquid, preferably a fuel, comprising the following steps:
1. Separation in Lab-on-a-chip of pdots precursors from a liquid, such as liquid fuel, to suppress the background fluorescence as well as to prevent pdots (fluorescent semiconducting polymer nanoparticles) from contamination with side molecules. This step can also be considered as a concentration of the pdot precursors from the fuel for further formation of pdot in the chip.
2. Batch-wise, continuous or semis-continuous formation of pdots in Lab-on-a-chip;
3. Detection of pdots fluorescence upon excitation, preferably performed in a continuous, automatic, in-line, in-situ mode (preferably inspector-free);
4. Optionally and preferably, control of pdots formation kinetics (pdots fluorescence vs. time and reagents addition) and use of these parameters for authentication (qualitative and quantitative analysis)

According to an embodiment of the present invention, a method is proposed to detect on a lab-on-chip detection device (427) a polymer marker (pdot precursor) dissolved in a liquid, preferably a fuel, wherein droplets of fuel containing the marker are injected into the LOC.

A special LOC design as well as addition of some specific chemical reagents in a chip enables the formation of pdots, which are collected in an optically transparent collector at the "exterior" of the chip, from where the luminescence is detected.

At the entry of the LOC, the non-aggregated fluorescent pdot precursor is present in a liquid, preferably a hydrophobic medium (fuel). At the exit of the chip, the self-assembled (aggregated) pdot is present in an aqueous solution or dispersion, which exhibits enhanced luminescent properties that can be red-shifted or blue-shifted compared to the pdot precursor, as explained above.

Automatic (semi-continuous or continuous, in-line, in-situ) detection of pdots fluorescence (qualitative and quantitative analysis with kinetics control) can be performed using a detector coupled with LOC. The marker analysis results may then be sent periodically to a central control system.

In order to separate the precursors from other organic components in the fuel, the chip contains a means that is suitable for this purpose. This is preferably a size and/or chemical affinity exclusion membrane, for example a PDMS (poly dimethyl siloxane) membrane. Such a membrane lets small molecules pass, such as hexane; however it retains larger molecules such as the Pdot precursors. Such step allows to pre concentrate the precursors. Consequently, it is possible to add a very small amount of said precursors in the fuel (less than 1 ppm).

According to an embodiment of the present invention, a method is proposed to detect on a lab-on-chip detection device (427) a pdot precursor dissolved in a liquid, preferably a fuel, comprising the following step:
Introducing a small amount of marked fluid, preferably less than 10 ml, into the lab-on-chip (427) at an entry (401) and via a microfluidic channel (402).

A channel can be added to the LOC containing a marker that will act as an energy acceptor of the emitted light from the first liquid marker (the pdot), further transforming that light thanks to the chip assembly, as discussed above and illustrated in FIG. 4.

The second marker (acceptor) can also be a semiconducting/conjugated polymer, but not necessarily. It can also be a conventional organic dye, or any kind of hydrophobic luminescent marker. It is crucial to have a spectral overlap between the emission of the first semiconducting polymer (energy donor) and the excitation of the second marker (energy acceptor). These two components can be considered as key and lock, and only the appropriate coupling gives the authentic answer.

According to an embodiment of the present invention, a method is proposed to detect on a lab-on-chip detection device (427) a polymer marker dissolved in a liquid, preferably a fuel, comprising the following step:
Analyzing the liquid fluorescence background of the introduced marked liquid at an exit (425).

Some fuel components are fluorescent. This "background" fluorescence may mask the target compounds (pdots), making highly selective and sensitive detection difficult. It is possible to overcome (at least partially) this problem by:
Tuning the emission of pdots to the region with low fluorescence background (for diesel and gasoline, emission at wavelengths >550 nm are preferable), and/or
separating within the LOC physically the fluorescent pdots precursors from the rest of the fuel and analyzing only the former.

According to an embodiment of the present invention, a method is proposed to detect on a lab-on-chip detection device (427) a polymer marker (pdot precursor) dissolved in a liquid, preferably a fuel, comprising the following step:
filtering the introduced marked liquid through a size and/or chemical affinity exclusion membrane (410), for example a PDMS (poly di methyl siloxane) membrane, in order to concentrate polymer and to produce a mixture A.

According to an embodiment of the invention, the LOC includes a separation section at the entry of the marked fuel into the chip. The separation is achieved with a membrane, such as a mesoporous membrane for size exclusions, or a PDMS membrane for chemical affinity exclusion. For example, a PDMS membrane exhibits different permeability towards different hydrophobic species, such as hexane, toluene or semiconducting polymers. It can efficiently separate some of the components from the Pdots precursors to be transferred further in the LOC for the Pdot formation.

Another possibility (alternative to a membrane) is to use centrifugal forces, in order to separate large molecules from other components of fuel. Preferably, the membrane and the size exclusion approach is used.

According to an embodiment of the present invention, a method is proposed to detect on a lab-on-chip detection device (427) a polymer marker (pdot precursor) dissolved in a liquid, preferably a fuel, comprising the following step:
Introducing into the lab-on-chip (427) at an entry (415) a small amount of water, preferably in an amount <10 ml, to be added to mixture A, in order to promote the self-assembly of the polymer and to form pdots.

To achieve formation of pdots in LOC (i.e., self-assembly of pdot precursor), two procedures can be used, mini-emulsion or re-precipitation, as described above. For both procedures, the LOC comprises appropriate microfluidic channels 402 and chambers where reagents mix and react.

The channel network can be obtained by patterning a photopolymeric layer or by micromachining of silicon, glass or plastic substrates.

The fuel flows into the channel reaching the reaction and the detection areas (which can also be obtained in the same chamber). Wetting and anti-wetting surface properties help the flow motion inside the hydraulics circuit.

The LOC 427 can be realized in glass, plastic or quartz, to have the possibility to perform the fluorescent analysis. In general, also a lab-on-chip controller is provided that is configured to control any one of the LOC elements so as to implement and perform any method embodiment as part of the present disclosure. More specifically, the LOC controller may be configured to operate one or more of the below mentioned valves and/or elements so as to effect the analysis stages on the LOC. It is to be noted, however, that not all steps and stages as mentioned in the present examples are necessary to implement an embodiment of the present invention. In particular, the stages of (a) passing the liquid through membrane (410) and of produce a first mixture (A); (b) adding an amount of organic solvent to the first mixture (A); (c) adding an amount of water to the first mixture (A); (d) heating the second mixture; (e) filtering the concentrated second mixture; and (f) collecting and transporting the pdots may already suffice for attaining the advantages of the embodiments of the present invention.

According to an embodiment of the present invention, a method is proposed to detect on a lab-on-chip detection device (427) a polymer marker (pdot precursor) dissolved in a liquid, preferably a fuel, comprising the following step:
concentration of the pdot precursors in the fuel;
extraction or dissolution of the pdot precursors from a membrane with appropriate solvent (e.g. THF for re-precipitation, e.g. toluene for min-emulsion),
pdot formation;
concentration of Pdots;
collection of Pdots.

With reference to the LOC 427 in FIG. 3, the five different phases can be so described and carried out. The following is merely an Example how the method can be carried out, and other setups can be used with the present invention.

Phase 1: Concentration of Markers in Fuel
Valves 405, 407 are closed, valve 404 is open. Pdot precursors and heavy fuel elements are captured in the membrane Phase 2: Extraction of Pdot Precursors from Membrane with Appropriate Solvent
Valves 404, 405 are closed, valves 407, 408 are open to purge fuel back to the membrane. Then valve 408 is closed, valve 405 is opened.

Phase 3: Re-Precipitation
LOC controller opens valves 413, 416, 418, 420.

Phase 4: Concentration of Pdots from Solvent+Water
LOC controller closes valve 418, and opens valve 424.

Phase 5: Extraction of Pdots from Membrane
LOC controller closes valve 420 and 424, and opens valves 418 and 421.

During the process Valve 403 is always closed except to collect fuel background.

Rinsing of the whole circuit is preferably carried out.

With reference to the LOC 427 in FIG. 3, the inventive method can be so described and carried out in a working example of the invention:

In this Example, the fuel is marked with 1 ppm of conjugated polymer 101.

In the beginning, all valves are closed. 6 ml of fuel are introduced into the chip at the entry 401 and via the microfluidic channel 402.

First, only 403 valve is open, and 1 ml of the introduced marked fuel is passed through the channel 402. The real fuel background is analyzed at the exit 425. Valve 403 is closed.

In a second step valves 404 and 408 are opened, and 5 ml of marked fuel are let pass through the PDMS membrane 410. The fuel with reduced concentration of conjugated polymers is collected at the exit 409.

Then valve 404 is closed and valve 407 is opened and 1 ml of THF is flowed to exit 409 via the entry 406 to purge the dead volume behind the membrane 410.

Then valve 408 is closed and valve 405 is opened, and 0.1 ml of THF is introduced into the chip via entry 406. Valve 407 is closed.

It follows the closing of valve 405 and opening of valve 413. Through entry 412, 2 ul of PSMA in THF (concentration of the solution is 10 ppm) are introduced. Valve 413 is then closed.

The mixture passes through channel 411 where it is being homogenized. Valve 416 is opened and about 0.3 ml of water is introduced via entry 415. Valve 416 is closed.

The mixture flows over a local heating region 417. Such heating step is optional. Then valves 420 and 424 are opened, while valves 418 and 421 are closed. "Free" THF and water are collected in a reservoir 423, while being cooled at the local cooling plate 426, and aimed for recycling.

The size-exclusion membrane 428 retains the formed Pdots. Then valves 424 and 420 are closed, and valve 421 is opened. Pure water is introduced via entry 422. Valve 418 is opened, the Pdots are collected via collector 419.

Valve 421 is closed and finally valve 418 is closed and the solution is analyzed.

According to an embodiment of the present invention, a method is proposed to detect on a lab-on-chip detection device (427) a pdot precursors dissolved in a liquid, preferably a fuel, comprising the following step:
Analyzing the so obtained aqueous dispersion B in the collector (419, 509) with a fluorescence detecting device (502), preferably a spectrometer or silicon photodiode, in order to detect the so extracted and produced Pdots and their fluorescence.

Once the Pdots are formed and accumulated or continuously flowed in a cuvette 509 from the inflow pipe 506 and an outflow pipe 507 and separated from the fuel, therefore in aqueous solution, they can be detected by fluorescence using the following steps (see FIG. 3):
Light excitation in a suitable wavelength in the range 300-500 nm. The excitation source 501 can be a Light Emitting Diode (LED) with a relatively broad emission spectrum (typically 20-30 nm band width) or a laser, preferably a Laser Diode (LD) which has a narrow emission spectrum.
The light excitation 501 is directed and concentrated towards the detection zone (cuvette 509), in order to irradiate as much as possible the whole accumulation volume where the Pdots were collected. Guiding the light beam can be made classically using a lens arrangement, but for LOC 508, where the cuvette is relatively small (mm scale or below) and of typically parallelepiped or cuboid shape, an optical fiber light guide 510 is preferred. The light guide 510 can be of rectangular cross section to match the cuvette 509 cross section and hence optimize the light coupling efficiency. The light guide can be formed directly on the Lab on Chip 508 and be an integral part of it, the light source 501 (LED or LD) being located outside the LOC 508, preferably on the edge (see FIG. 4). This allows the LOC board 508 to be disposable, whereas the light source is kept. In a preferred embodiment the light guide is tapered to allow better coupling efficiency on the light source side.

Detection of the fluorescence emission from the excited Pdots using a light collection lens or lens arrangement 505, located out of the LOC 508 plane, which concentrates the fluorescent light beams onto a detector. A suitable long-pass filter 504 is positioned either in front of the lens or in front of the detector to cut off the elastic scattered light from the irradiation source.

The detector can also be equipped with a band-pass filter 504 tuned to the Pdot emission spectrum to further favor the detection of their fluorescence with respect to any other background fluorescence or elastic scattering. This makes the detector specifically sensitive to the Pdot emission and allows authentication by discrimination.

The detector itself can be a simple Silicon Photodiode (PD) with an electronic amplifier. In case the Pdot concentration is low and hence the fluorescence signal also, an Avalanche Photodiode (APD) or a compact Photomultiplier tube can be used as detector.

In a preferred embodiment, a compact optical spectrometer 502 can be used to perform a spectral analysis of the Pdot fluorescence emission. This has the advantage of allowing the detection of different Pdot fluorescence spectra and to discriminate one from another, in case different Pdot spectral signatures are used to tag different liquids (fuels). The device can therefore be seen as a multipurpose fluorescence detector, with the capability to identify different spectral signatures and hence to identify the type of liquid (fuel) which is analyzed. Suitable algorithms can be used to allow discrimination of different Pdot spectral signatures from any fake tagging element and from the background fluorescence from the spectral signature shape and intensity.

The compact spectrometer 502 can be of planar grating type or a so-called flat-field spectrograph using aberration corrected holographic grating or any other type of compact spectrometer arrangement which can provide sufficient spectral resolution (typically 15 nm BW). In any case, the detector in the spectrometer is composed of a linear photodiode array (PDA) or a linear Charge Coupled Device (CCD) or a linear Complementary Metal Oxide Semiconductor (CMOS). The detector is characterized in that each light sensitive element (pixel) provides an electrical signal corresponding to a given portion of the light spectrum which allows measuring the wavelength dependent spectral fluorescence of the Pdots. When using a spectrometer, the fluorescence light collection scheme is particular in that the cuvette geometry can be matched to the entrance slit 503 of the spectrometer 502. The cuvette 509 aspect ratio can then be designed in order to match the aspect ratio of the spectrometer entrance slit 503 to optimized light collection efficiency.

In all the above embodiments, a quantitative fluorescence intensity measurement can be obtained by proper calibration of the detector using different known concentrations of the Pdot.

Control of pdots formation kinetics (pdots fluorescence vs. time and reagents addition) and use of these parameters for authentication (qualitative and quantitative marker analysis) can be performed thanks to the in line formation and in situ detection.

In one embodiment, the present invention provides a lab-on-chip detection device (427) suitable to detect a polymer capable of forming a semiconducting polymer dot (pdot) dissolved in a liquid, preferably a fuel, comprising:

an entry (401) and a microfluidic channel (402) for introducing an amount of liquid into the lab-on-chip (427);

an exit (425) for analyzing the liquid fluorescence background of the introduced liquid;

a size and/or chemical affinity exclusion membrane (410) for filtering the introduced marked liquid in order to increase the concentration of the polymer and to produce a mixture A;

an entry (406) for introducing into the lab-on-chip (427) an amount of organic solvent to be added to mixture A to dissolve and extract the Conjugated polymer;

optionally, an entry (412) for introducing into the lab-on-chip (427) an amount of a polymeric additive diluted in an organic solvent to be added to mixture A to functionalize the polymer;

optionally, a microfluidic channel (411) exhibiting mixing structure and/or capability for homogenizing the so obtained mixture A;

an entry (415) for introducing into the lab-on-chip (427) an amount of water, to be added to mixture A, in order to promote the aggregation of the polymer and to produce the pdots;

optionally, a local heating region (417) for heating the so obtained mixture A, in order to concentrate mixture A by evaporating the organic solvent;

a membrane (428), for example size-exclusion membrane, for filtering the so obtained mixture A, to retain the so formed Pdots on the membrane (428);

optionally, a reservoir (423) for collecting the so generated organic solvents and water free of Pdots, while being cooled at a local cooling plate (426);

an entry (422) for introducing into the lab-on-chip (427) a small amount of water, to collect the pdots retained on the membrane (428), in order to form an aqueous dispersion B comprising said pdots and to transport said pdots to a preferably optically transparent collector (419, 509) in the form of an aqueous dispersion B;

a fluorescence detecting device (502), preferably a spectrometer or silicon photodiode, for analyzing the so obtained aqueous dispersion B in the collector (419, 509), in order to detect the so extracted and produced Pdots and their fluorescence.

EXAMPLE 1

One embodiment of the method of the present invention is illustrated FIGS. 5 and 6:

3 ml of a marked fuel are introduced in a flask 601. To the flask are added 3 ml of a water-miscible solvent in which the marker is soluble, such as THF, in order to form the mixture 602 (see FIG. 5*a*). The flask is typically strongly agitated in order to ensure mixing of the sample and the solvent. The agitation mode is not limited; and any of manually, mechanically, with a magnetic stirrer, or ultrasonically can be used.

Then the solution is passed through a chemical affinity membrane, in particular a hydrophilic membrane 603, such as a nylon membrane with a porosity of about 0.2 microns. The organic liquid, such as fuel, 604 has low affinity to the nylon membrane and consequently does not cross the membrane 603, but remains on the top of the membrane 603.

Conversely, the water miscible solvent 605 (now containing the polymer 102), has good compatibility with the hydrophilic membrane 603 and crosses the membrane together with the non-aggregated polymer, see FIGS. 5 b) and c). The porosity of the membrane 603 is selected in order to let pass through the majority of the non-aggregated polymers.

In this embodiment, the solution 605 is divided into two parts. The first part is collected into a cuvette, and the luminescence thereof is measured. The second part is transferred to a flask, and 6 ml of water are added in order to form the mixture 606 (see FIG. 5d)). The mixture 606 is agitated, and again the agitation mode is not limited. At this stage, the polymer aggregates and forms dispersion 607 of polymer particles (pdots) dispersed in water (see FIG. 5 e)). The dispersion 607 is transferred to a cuvette and the luminescence is measured.

In this embodiment, the luminescence of 605 and 607 are compared. In one embodiment, the liquid is considered genuine if the peak maximum measured for the pdot in the dispersion 607 is shifted towards longer wavelengths as compared to the peak maximum measured for the non-aggregated polymer (pdot precursor) in the solution 605, for instance by 10 nm or more, as shown in FIG. 6.

In an alternative embodiment, the peak wavelength obtained from the pdot in the dispersion 607 may be shifted to shorter wavelengths, and a liquid may be considered genuine if the peak maximum measured for the pdot in the dispersion 607 is shifted toward shorter wavelengths as compared to the peak maximum measured for the non-aggregated polymer in the solution 605 by 10 nm or more.

In the above embodiment also illustrated in FIGS. 5 and 6, the solution 605 is divided into two parts, and the luminescence of the pdot precursor (polymer) and of pdot (aggregated polymer) are measured separately, and possibly simultaneously. Alternatively, one may measure the luminescence of the polymer (pdot precursor) in the solution 605 prior to the aggregation/pdot formation, and subsequently measure the luminescence of the pdot in the dispersion 607 after it has been formed. By comparing the luminescence measured for the pdot in the dispersion 607 with the (stored) luminescence of the polymer (pdot precursor) in the liquid 605, again a decision as to genuineness or non-genuineness of the liquid can be made, as outlined above.

The excitation wavelength used to measure the emission spectra of pdot precursors and pdots, as shown in FIGS. 6, 8 and 10, is 435 nm. The excitation is provided by the excitation monochromator of a spectrofluorometer using a Xenon Arc lamp. The excitation with a blue LED is also suited, for example a blue LED centered at 450 nm with FWHM of 20-50 nm.

EXAMPLE 2

Another embodiment of the method of the present invention is illustrated in FIGS. 7 and 8:

Similar as in Example 1, 3 ml of a marked fuel are introduced in a flask 601. To the flask are added 3 ml of a water miscible solvent in which the marker is soluble, such as THF, in order to form the mixture 602 (see FIG. 7 a) and b)).

The flask is agitated. The agitation mode is not limited and can be suitably selected, such as from manually, mechanically, with a magnetic stirrer, or ultrasonically. Then the solution is passed through a chemical affinity membrane 603, such as a hydrophilic membrane 603, for instance a nylon membrane with a porosity of about 0.2 microns (see FIG. 7c)). The organic liquid such as fuel 604 has poor affinity with the nylon membrane and consequently does not cross the membrane 603, but remains on the top of the membrane 603.

On the other hand, the solution of the water miscible solvent 605 now containing the polymer 102 (pdot precursor) is compatible with the hydrophilic membrane 603 and crosses the membrane, including the polymer (pdot precursor). The porosity of the membrane 603 is selected in order to let pass through the majority of the non-aggregated polymers.

In this embodiment, the solution 605 is divided into two parts. The first part is transferred to a cuvette, and the luminescence thereof is measured. The second part is transferred to a flask to which are added 6 ml of water in order to form the mixture 606 (see FIG. 7d)). The mixture 606 is agitated, with no limitation on the agitation mode, leading to precipitation and aggregation of polymer particles (pdots).

The mixture 606 is then filtered through a size exclusion membrane, for example a nylon membrane with porosity of about 0.2 microns. The aggregated polymer (pdots) 608 are retained on the top of the membrane 603, while the mixture 609 of water and water-miscible solvent passes through the membrane (see FIG. 7e)).

The membrane 603 with the isolated pdots 608 is recovered, and the luminescence of the pdots is measured. Here, the membrane 603 serves as a support for the dots 608 whose luminescence is measured.

Then, the luminescence measured for the polymer (pdot precursor) in the solution of 605 and for the pdot 608 are compared. The fuel is considered genuine if a predetermined difference between the measured luminescences exists. This difference may for instance be that the peak maximum measured for the luminescent emission of pdot 608 is shifted toward higher wavelengths as compared to the peak maximum measured for the luminescent emission of the polymer (pdot precursor) in the solution 605, e.g. by 10 nm or more, as shown in FIG. 8.

The difference in the peak maxima may also be greater than 10 nm, such as 20, 30, or 50 nm, as illustrated in FIG. 8. This allows for using a device having a lower spectral resolution for determining the genuineness of the liquid.

EXAMPLE 3

Another embodiment of the method of the present invention is illustrated in FIGS. 9 and 10:

Again, 3 ml of a fuel containing the pdot precursor are introduced in a flask 601. To the flask are added 3 ml of a water miscible solvent in which the pdot precursor is soluble, such as THF, in order to form the mixture 602 (see FIG. 9a))

The flask is agitated, wherein the agitation mode is not limited and be selected from manually, mechanically, with a magnetic stirrer, or ultrasonically. Then the solution is passed through a chemical affinity membrane, in particular hydrophilic membrane 603, such as a nylon membrane with a porosity of about 0.2 microns (see FIG. 9 b)). The fuel 604 has low affinity to the nylon membrane, and consequently does not cross the membrane 603 but remain on the top of the membrane 603. On the other hand, the water miscible solvent 605 containing the pdot precursor has a good compatibility with the hydrophilic membrane 603 and crosses the membrane together with the polymer.

Then, in this embodiment, the solution 605 containing the pdot precursor is divided into two parts (see FIG. 9 d) and e)) The first part is directly filtered through a size exclusion membrane 610 with a porosity of about 0.2 or 0.1 microns. The porosity of the membrane is selected in order to retain traces of non-aggregated polymer. The membrane 610 with traces of pdot precursor (polymer) 611 is recovered, and the luminescence of the non-aggregated polymer 611 is measured.

The second part is transferred to a flask to which are added 6 ml of water, to thereby form the mixture 606 (see FIG. 9e)). The mixture 606 is agitated, wherein the agitation mode is not limited, to thereby precipitate and aggregate the pdot precursor for forming the pdots.

The mixture 606 is then filtered through a size exclusion membrane 603, for example a nylon membrane with porosity of about 0.2 microns (see FIG. 9f)). The pdots 608 are retained on the top of the membrane 603, while the mixture 609 of water and water-miscible solvent passes through the membrane.

The membrane 603 with pdots 608 is recovered and the luminescence of the pdots is measured. Here, the membrane 603 serves as a support on which are deposited the pdots 608 whose luminescence is measured.

Then, the luminescence obtained from the polymer 611 and from the pdots 608 are compared (see FIG. 10). The fuel is considered genuine if a predetermined criterion is met, e.g. that the peak maximum of the measured luminescence from the pdots 608 is shifted toward longer (or shorter) wavelengths as compared to the peak maximum of the measured luminescence from the polymer 611 by 10 nm or more, as shown in FIG. 10.

Methods of authentication described in examples 1, 2 and 3 can be obtained in a flask as represented in FIGS. 5, 7 and 9, but they can also be obtained in a Lab on a Chip as represented in FIG. 11.

For the Example 1 (FIG. 5), the corresponding LOC operates as following.
i. all the valves of the LOC 710 are closed
ii. the marked fuel is introduced via entry 701 and channel 702
iii. THF is introduced via entry 705 thanks controlled with valve 706
iv. the chemical affinity membrane 709 separate fuel from THF and non-aggregated polymers
v. fuel is removed via exit 707 controlled by valve 708
vi. the solution of non-aggregated polymers in THF is collected in 704 and the luminescence of non-aggregated polymers is masured
vii. the valve 711 is opened and the solution of non-aggregated polymers enters the mixing region 712
viii. optionally, some polymeric additives of surfactants can be introduced via entry 713 controlled with valve 714
ix. water is introduced via 715 controlled with valve 716 and the pdots start to form
x. valve 717 and 719 are opened and the pdots are retained on the size exclusion membrane 718
xi. valves 717 and 719 are closed and 722 and 723 are opened
xii. water is introduced via entry 721 and the dispersion in water of pdots are collected on exit 724.
xii. the luminescence of collected pdots in water is measured and compared to the luminescence of non-aggregated polymers

The invention claimed is:
1. A method for authenticating the genuineness and/or origin of a liquid comprising a polymer capable of forming a semiconducting polymer particle (pdot), comprising the steps
   i. concentrating, isolating and/or extracting a polymer capable of forming a semiconducting polymer particle (pdot);
   ii. aggregating the polymer obtained in Step i. to form semiconducting polymer dots (pdots);
   iii. irradiating the formed pdots with electromagnetic radiation capable of exciting the pdots to emit electromagnetic radiation by fluorescence and/or phosphorescence, and
   iv. observing electromagnetic radiation emitted in response to the exciting irradiation of step iii, wherein if the observed electromagnetic radiation conforms to a parameter that is defined as indicative for the genuineness and/or origin of the liquid, a decision as to the authenticity and/or origin of the liquid is made.
2. The method according to claim 1, wherein the liquid is a fuel and wherein the concentration of the polymer capable of forming a semiconductor particle is equal to or less than 10 ppm by weight.
3. The method according to claim 1, wherein the method is implemented in a portable device.
4. The method according to claim 1, wherein the aggregation of the polymer to form pdots is performed by re-precipitation using water and a water-miscible organic solvent; or by mini-emulsion using two or more non-miscible solvents and a surfactant.
5. The method according to claim 1, which additionally comprises the following steps:
   iii.a. irradiating the polymer capable of forming a semiconducting polymer particles, or a solution containing it, with electromagnetic radiation capable of exciting the polymers to emit electromagnetic radiation by fluorescence and/or phosphorescence, and
   iv.a. observing the electromagnetic radiation emitted in response to the exciting irradiation of step iii.a.
6. The method according to claim 5, which comprises further a step of comparing the electromagnetic radiation emitted by the polymer observed in step iv.a with the electromagnetic radiation emitted by the pdot observed in step iv.
7. The method according to claim 5, wherein the polymer irradiated in step iii.a is present in a liquid to be evaluated for its genuineness and/or origin, is present in a water-soluble solvent other than the liquid to be evaluated for its genuineness and/or origin, or is present undissolved on a supporting surface.
8. The method according to claim 1, wherein the polymer capable of forming a semiconducting polymer dot (pdot) contains a structural unit selected from structural units comprising a (9, 9, dioctyl-2,7-divinylenefluorenylene)-alt-co-(9,10-anthracene) moiety of formula (1) and structural units comprising a moiety of formula (102):

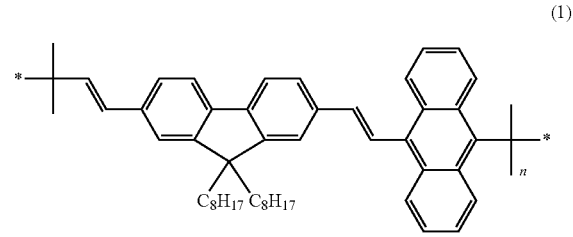

(1)

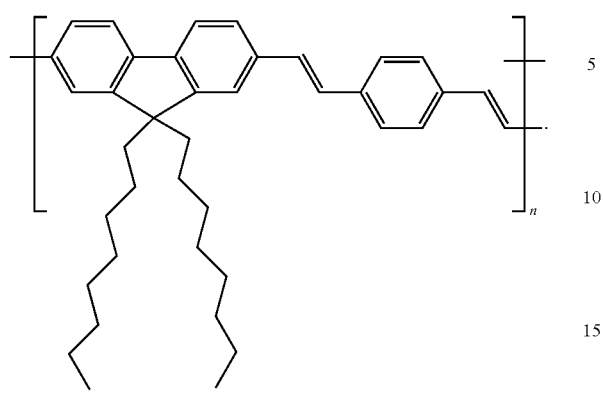
(102)
* * * * *